United States Patent [19]

Sofranko et al.

[11] Patent Number: 4,547,610
[45] Date of Patent: Oct. 15, 1985

[54] METHANE CONVERSION

[75] Inventors: John A. Sofranko, Malvern; Howard P. Withers, Jr., Douglassville, both of Pa.

[73] Assignee: Atlantic Richfield Company, Los Angeles, Calif.

[21] Appl. No.: 669,551

[22] Filed: Nov. 8, 1984

Related U.S. Application Data

[63] Continuation-in-part of Ser. No. 600,658, Apr. 16, 1984, abandoned.

[51] Int. Cl.$^4$ ................................................ C07C 2/00
[52] U.S. Cl. .................................... 585/500; 585/415; 585/417; 585/418; 585/541; 585/654; 585/656; 585/658; 585/661; 585/700; 585/943
[58] Field of Search ............... 585/417, 418, 415, 500, 585/654, 656, 658, 661, 541, 943, 700

[56] References Cited

U.S. PATENT DOCUMENTS 4,205,194  5/1980  Mitchell et al. ..................... 585/500

OTHER PUBLICATIONS

Fang, T. et al., "Catalytic Pyrolysis of Methane," J. Chinese Chem. Society, 29, 265–273, 1981.

Primary Examiner—William R. Dixon, Jr.
Assistant Examiner—Cynthia A. Prezlock
Attorney, Agent, or Firm—Craig E. Larson

[57] ABSTRACT

An improved method for converting methane to higher hydrocarbon products by contacting a gas comprising methane and a reducible metal oxide under synthesis conditions, the improvement which comprises performing the contacting in the presence of oxides of nitrogen. Nitrous oxide is a preferred nitrogen oxide.

9 Claims, No Drawings

METHANE CONVERSION

CROSS-REFERENCE TO RELATED CASE

This application is a continuation-in-part of U.S. patent application Ser. No. 06/600,658, filed Apr. 16, 1984, abandoned.

BACKGROUND OF THE INVENTION

This invention relates to the synthesis of hydrocarbons from a methane source. A particular application of this invention is a method for converting natural gas to more readily transportable material.

A major source of methane is natural gas. Other sources of methane have been considered for fuel supply, e.g., the methane present in coal deposits or formed during mining operations. Relatively small amounts of methane are also produced in various petroluem processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons carbons although some ethane may be included. Gas conditioning is required to alter the composition of wellhead gas, processing facilities usually being located in or near the production fields. Conventional processing of wellhead natural gas yields processed natural gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extension safety precautions. Transport of natural gas has been a continuing problem in the exploitation of natural gas resources. It would be extremely valuable to be able to convert methane (e.g., natural gas) to more readily handleable or transportable products. Moreover, direct convesion of olefins such as ethylene or propylene would be extremely valuable to the chemical industry.

Recently, it has been discovered that methane may be converted to higher hydrocarbons (e.g., ethane, ethylene and higher homologs) by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regenerating a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See commonly-assigned U.S. Pat. Nos. 4,443,649; 4,444,984; 4,443,648; 4,443,645; 4,443,647; 4,443,644; and 4,443,646 the entire contents of each being incorporated herein by reference.

Commonly-assigned U.S. patent application Ser. No. 522,935, filed Aug. 12, 1983, discloses and claims a process which comprises contacting methane with an oxidative synthesizing agent under elevated pressure (e.g., 2–100 atmospheres) to produce greater amounts of $C_3+$ hydrocarbon products.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

Commonly-assigned U.S. Pat. No. 4,499,322, discloses and claims a process for the conversion of methane to higher hydrocarbons which comprises contacting methane with an oxidative synthesizing agent containing a promoting amount of alkali metal and/or compounds thereof. The entire content of this patent is incorporated herein by reference.

Commonly-assigned U.S. Pat. No. 4,485,374 discloses and claims a process for the conversion of methane of higher hydrocarbons which comprises contacting methane with an oxidative synthesizing agent containing a promoting amount of alkaline earth metal and/or compounds thereof. The entire content of this patent is incorporated herein by reference.

Commonly-assigned U.S. Pat. No. 4,499,323 discloses and claims a process for the conversion of methane to higher hydrocarbons which comprises contacting methane with a contact solid comprising a reducible oxide of praseodymium and at least one member of the group consisting of alkali metals, alkaline earth metals, and compounds thereof. The entire content of this patent is incorporated herein by reference.

Commonly-assigned U.S. patent application Ser. No. 06/600,918 discloses and claims a process for the conversion of methane to higher hydrocarbons which comprises contacting methane with a contact solid comprising a reducible oxide of terbium and at least one member of the group consisting of alkali metals, alkaline earth metals, and compounds thereof. The entire content of this application is incorporated herein by reference.

Commonly-assigned U.S. Pat. No. 4,499,324 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof. The entire content of this patent is incorporated herein by reference.

Commonly-assigned U.S. patent application Ser. No. 06/600,730 discloses and claims a process for the conversion of methane to higher hydrocarbons which comprises contacting methane with a contact solid comprising a reducible oxide of iron and at least one member of the group consisting of alkali metals, alkaline earth metals, and compounds thereof. The entire content of this application is incorporated herein by reference.

Commonly-assigned U.S. Pat. No. 4,489,215 discloses and claims a process for the conversion of methane to higher hydrocarbons which comprises contacting methane with a contact solid comprising a reducible oxide of ruthenium and at least one member of the group consisting of alkali metals, alkaline earth metals, and compounds thereof. The entire content of this patent is incorporated herein by reference.

As noted, the reaction products of such processes are mainly ethylene, ethane and other light hydrocarbons, carbon oxides, coke and water. It would be beneficial in these processes to reduce selectivities to carbon oxides and coke and to increase methane conversions to the desired hydrocarbon products.

Accordingly, an object of this invention is to provide an improved process for converting methane to higher hydrocarbons wherein methane is contacted with a reducible metal oxide as a selective oxygen source. Other aspects, objects and the several advantages of this invention will become apparent to those skilled in the art upon reading this disclosure and the appended claims.

SUMMARY OF THE INVENTION

It has now been found that the conversion of methane to higher hydrocarbons wherein a gas comprising methane is contacted with contact solid comprising a reducible metal oxide may be improved by performing said contacting in the presence of a gas comprising oxides of nitrogen. Nitrous oxide ($N_2O$) is a presently preferred oxide of nitrogen. Thus, the conversion of methane to higher hydrocarbons may be improved by contacting a first, hydrocarbon gas comprising methane and a second gas comprising at least one oxide of nitrogen with at least one reducible oxide of at least one metal which oxide(s) when contacted with methane at methane conversion conditions (preferably at a temperature within the range of about 500° to 1000° C.) and reduced and produce higher hydrocarbon products and water.

Preferred reducible oxides include oxides of metals selected from the group consisting of Mn, Sn, In, Ge, Pb, Sb and Bi. Preferred reducible oxides also include oxides of metals selected from the group consisting of Pr, Tb and Ce and oxides of metals selected from the group consisting of Fe and Ru. More preferred are reducible oxides of Mn, Pr and/or Tb. Reducible oxides of Mn are particularly preferred.

The reducible oxides may be promoted by alkali or alkaline earth metals or compounds thereof. Alkali metals are selected from the group consisting of Li, Na, K, Rb and Cs. Alkaline earth metals are selected from the group consisting of Mg, Ca, Sr and Ba. Sodium is a preferred promoter.

The stability of the promoted reducible metal oxides may be enhanced by incorporating phosphorus into the composition.

DETAILED DESCRIPTION OF THE INVENTION

In addition to methane the hydrocarbon feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The gas comprising oxides of nitrogen may be any of a wide number of materials. Suitable oxides of nitrogen include $N_2O$, $NO$, $N_2O_3$, $N_2O_5$ and $NO_2$. Nitrous oxide ($N_2O$) is presently preferred. It is also within the scope of the present invention to employ a nitrogen-containing compound which generates oxides of nitrogen under the conditions of the present process.

The ratio of hydrocarbon feedstock to the gas comprising oxides of nitrogen ($NO_x$) is not narrowly critical to the present invention. It is desirable to control the ratio to avoid the formation of gaseous mixtures within the flammable region. The volume ratio of hydrocarbon to $NO_x$ is preferably within the range of about 0.1–100:1, more preferably within the range of about 1–50:1. Methane/$N_2O$ feed mixtures containing about 30 to 90 volume % methane are desirable feedstreams.

The solid which is contacted with methane in method of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes (1) one or more oxides (i.e., compounds described by the general formula $M_xO_y$ wherein M is a metal and the subscripts x and y designate the relative atomic proportions of metal and oxide in the composition) and/or (2) one or more oxygen-containing metal compounds, provided that such oxides and compounds have the capability of performing to produce higher hydrocarbon products as set forth herein.

Effective agents for the conversion of methane to higher hydrocarbons have previously been found to comprise reducible oxides to metals selected from the group consisting of manganese, tin, indium, germanium, antimony, lead, bismuth and mixtures thereof.

Reducible oxides of cerium, praseodymium, and terbium have also been found to be effective for the conversion of methane to higher hydrocarbons, particularly when the rare earth component is associated with an alkali or alkaline earth metal component.

Reducible oxides of iron and ruthenium are also effective for the conversion of methane to higher hydrocarbons, particularly when associated with an alkali or alkaline earth metal.

The contact solid employed in the processs of the present invention may contain, in addition to the reducible metal oxide component, at least one alkali or alkaline earth metal or compounds thereof. The atomic ratio in which these materials are combined to form the contact solid is not narrowly critical. However, the preferred atomic ratio of the reducible oxide component (expressed as the metal, e.g., Mn) to the alkali/alkaline earth metal component (expressed as the metal, e.g., Na) is within the range of about 0.1–100:1, more preferably within the range of about 0.3–10:1.

The contact solid may optionally contain at least one phosphorus component. The amount of the phosphorus contained in the contact solid is again not narrowly critical. The atomic ratio of phosphorus to the reducible oxide component (expressed as the metal, e.g., Mn) is preferably less than about 2:1. More preferably, this ratio is within the range of about 0.1–5:1.

One preferred contact solid used in the process of this invention may be further expressed by the following empirical formula:

$$A_a B_b P_c O_d$$

wherein A is selected from the group consisting of Mn, Sn, In, Ge, Pb, Sb, Bi, and mixtures thereof; B is selected from the group consisting of alkali metals, a to d indicate the atomic ratio of each component; and when a is 10, b is within the range of about 1–33, c is within the range of about 0–20, and d has a value which is determined by the valence and proportions of the other elements present.

The foregoing components of the contact solid may be associated with support materials such as silica, alumini, titania, magnesia, zirconia and the like and combinations thereof. When employing agents containing rare earth components—oxides of Ce, Pr, and Tb—the rare earth oxides preferably serve as supports.

Reducible oxides of manganese have been found to be particularly desirable for methane conversion according to the method of the present invention. Particularly preferred agents comprise silica- or magnesia-supported solids containing oxides or manganese and sodium.

The contact solid can be prepared by any suitable method. Conventional methods such as precipitation, coprecipitation, impregnation or dry mixing can be used. supported solids may be prepared by methods such as adsorption, impregnation, precipitation, coprecipitation, and dry mixing can be used. When phosphorus is incorporated into the agent, it is desirable to provide it in the form of a phosphate of an alkaline metal or alkaline earth metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined, preferably in air, at a temperature within the range of about 300° to 1200° C. Particular calcination temperatures will vary depending upon the particular metal compound or compounds employed.

Regardless of how the components of the agent are combined, the composite will be dried and calcined at elevated temperatures prior to use of the process of this invention.

Preferably, methane and nitrogen oxides are contacted with the agent in the substantial absence of catalytically effective nickel, noble metals and compounds thereof. (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the method of this invention relative to such contacting in the absence of such metals and compounds thereof.

Operating temperatures for the method of this invention are generally within the range of about 300° to 1200° C., more preferably within the range of about 500° to 1000° C. Best results for contact solids containing manganese have been found at operating temperatures within the range of about 800° to 900° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressures of methane and nitrogen oxides effect overall results. Preferred operating pressures are within the range of about 0.1 to 30 atmospheres.

The space velocity of the gaseous reaction streams are similarly not critical to the presently claimed invention, but have been found to effect overall results. Preferred total gas hourly spaced velocities are within the range of about 10 to 100,000 hr.$^{-1}$, more preferably within the range of about 600 to 40,000 hr$^{-1}$.

Contacting methane and a reducible metal oxide to form higher hydrocarbons from methane also produces coproduct water and reduces the metal oxide. The exact nature of the reduced metal oxides are unknown, and so are referred to as "reduced metal oxides". Regeneration of reducible metal oxides in the method of the present invention occurs "in situ"—by contact of the reduced metal oxide with the nitrogen oxides cofed with methane to the contact zone.

The contact solids may be maintained in the contact zone as fixed, moving, or fluidized beds of solids. A fixed bed of solids is currently preferred for the method of this invention.

The effluent from the contact zone contains higher hydrocarbon products (e.g., ethylene, ethane and other light hydrocarbons), carbon oxides, water, unreacted hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

The invention is further illustrated by reference to the following Example.

EXAMPLE

A contact solid comprising a reducible oxide of manganese was prepared by impregnating magnesia with sodium permanganate, the amount of manganese providing being sufficient to yield a solid containing the equivalent of 12.5 wt. % NaMnO$_4$MgO. The impregnated solids were dried at 110° C. for four hours and then calcined in air in 800° C. for 16 hours. A quartz tube reactor (12 mm. inside diameter) was charged with 10 c.c (10.78 grams) of the solids. A series of runs were performed with CH$_4$/N$_2$O blends of various N$_2$O concentrations. The duration of each of these runs was 10 minutes. Results reported below in the Table include conversions and selectivities calculated on a carbon mole basis.

TABLE

| RUN # | Temp. | CH₄ GHSV | % N₂O IN CH₄ | % CH₄ CONV. | % Selectivity to: | | | | | | |
|---|---|---|---|---|---|---|---|---|---|---|---|
| | | | | | $C_2^=$ | $C_2$ | $C_3^=$ | $>C_4^=$ | CO | $CO_2$ | $C_2^+$ |
| 1 | 700° C. | 900 | 10 | 2.2 | 13.3 | 72.8 | 1.2 | 0 | 0 | 12.4 | 87.3 |
| 2 | 750° C. | 900 | 10 | 7.5 | 33.8 | 47.7 | 4.8 | 1.7 | 0 | 11.9 | 88.0 |
| 3 | 800° C. | 900 | 10 | 15.8 | 44.2 | 26.8 | 5.9 | 5.5 | TR | 17.6 | 82.3 |
| 4 | 800° C. | 1800 | 10 | 9.9 | 38.9 | 42.3 | 5.1 | 2.3 | TR | 11.3 | 88.6 |
| 5 | 750° C. | 900 | 20 | 12.0 | 37.0 | 40.0 | 5.4 | 2.2 | 0 | 15.4 | 84.6 |
| 6 | 800° C. | 900 | 20 | 19.0 | 42.9 | 21.8 | 5.5 | 6.1 | TR | 23.7 | 76.3 |
| 7 | 800° C. | 1800 | 20 | 15.3 | 41.3 | 33.8 | 5.4 | 3.2 | TR | 16.3 | 83.7 |
| 8 | 700° C. | 900 | 30 | 4.4 | 13.9 | 59.8 | 3.4 | 0.8 | TR | 22.2 | 77.9 |
| 9 | 750° C. | 900 | 30 | 13.1 | 37.7 | 37.0 | 5.4 | 2.0 | TR | 17.9 | 82.1 |
| 10 | 800° C. | 900 | 30 | 24.1 | 41.5 | 19.3 | 5.1 | 5.1 | TR | 29.3 | 70.7 |
| 11 | 800° C. | 1800 | 30 | 18.4 | 43.1 | 31.1 | 5.5 | 3.8 | TR | 16.5 | 83.5 |
| 12 | 700° C. | 900 | 40 | 6.9 | 24.5 | 44.0 | 3.1 | 0 | TR | 28.4 | 71.6 |
| 13 | 750° C. | 900 | 40 | 19.4 | 41.6 | 31.2 | 5.8 | 1.9 | 4.9 | 14.6 | 80.5 |
| 14 | 800° C. | 900 | 40 | 34.3 | 38.9 | 11.5 | 4.7 | 4.4 | 2.1 | 38.4 | 59.5 |
| 15 | 800° C. | 1800 | 40 | 24.1 | 44.0 | 20.8 | 5.6 | 4.0 | 4.0 | 21.4 | 74.5 |
| 16 | 700° C. | 900 | 50 | 6.1 | 7.5 | 55.1 | 3.9 | 2.9 | 2.8 | 27.6 | 69.4 |
| 17 | 750° C. | 900 | 50 | 21.0 | 38.0 | 27.3 | 5.2 | 1.5 | 6.4 | 21.6 | 72.0 |
| 18 | 800° C. | 900 | 50 | 36.7 | 36.9 | 10.9 | 4.2 | 3.6 | 4.5 | 40.1 | 55.3 |
| 19 | 800° C. | 1800 | 50 | 28.4 | 41.1 | 19.2 | 4.6 | 3.1 | 4.9 | 27.1 | 67.9 |
| 20 | 800° C. | 2700 | 50 | 15.0 | 33.5 | 33.7 | 4.6 | 1.5 | 13.6 | 13.1 | 73.3 |
| 21 | 825° C. | 2700 | 50 | 28.3 | 41.6 | 18.7 | 4.9 | 3.1 | 6.1 | 25.8 | 68.2 |
| 22 | 825° C. | 3600 | 50 | 22.1 | 42.0 | 24.6 | 4.3 | 2.6 | 6.9 | 19.7 | 73.4 |
| 23 | 825° C. | 2700 | 40 | 29.2 | 43.9 | 16.4 | 5.1 | 3.9 | 3.4 | 27.3 | 69.3 |
| 24 | 825° C. | 3600 | 40 | 19.3 | 45.3 | 26.3 | 5.6 | 3.5 | 5.0 | 14.4 | 80.6 |

What is claimed is:

1. In a method for converting methane to higher hydrocarbon products wherein a gas comprising methane is contacted at a temperature selected within the range of 500° to 1000° C. with at least one reducible oxide of at least one metal which oxides when contacted with methane at said temperature are reduced and produce higher hydrocarbon products and water, the improvement which comprises performing said contact in the presence of a gas comprising at least one oxide of nitrogen.

2. The method of claim 1 wherein said oxides of nitrogen are selected from the group consisting of N₂O, NO, N₂O₃, N₂O₅, NO₂ and mixtures thereof.

3. The method of claim 1 wherein said oxides of nitrogen comprise N₂O.

4. The method of claim 1 wherein said reducible metal oxide is selected from the group consisting of Mn, Sn, In, Ge, Pb, Sb, Bi, Pr, Tb, Ce, Fe and Ru.

5. The method of claim 4 wherein said reducible metal oxides are associated with at least one promoter selected from the group consisting of alkali metals, alkaline earth metals and compounds thereof.

6. The method af claim 4 wherein said reducible metal oxides are associated with a support material.

7. The method of claim 6 wherein said support comprises silica.

8. The method of claim 6 wherein said support comprises magnesia.

9. The method of claim 1 wherein said metal is manganese.

* * * * *